United States Patent [19]

Johansen

[11] 4,340,675
[45] Jul. 20, 1982

[54] PROCESS FOR RECOVERING Cu,Zn-SUPEROXIDE DISMUTASE FROM YEAST

[75] Inventor: Jack T. Johansen, Rungsted Kyst, Denmark

[73] Assignee: De Forenede Bryggerier A/S, Copenhagen, Denmark

[21] Appl. No.: 149,392

[22] Filed: May 13, 1980

[30] Foreign Application Priority Data

May 17, 1979 [DK] Denmark .............................. 2033/79

[51] Int. Cl.$^3$ .............................................. C12N 9/02
[52] U.S. Cl. ...................................... 435/189; 435/259
[58] Field of Search ................ 435/189, 259, 814, 815

[56] References Cited

U.S. PATENT DOCUMENTS 3,758,682  9/1973  Huber et al. ..................... 260/112 B

FOREIGN PATENT DOCUMENTS 131091  3/1975  Denmark .

OTHER PUBLICATIONS

Goscin et al. in Biochimica et Biophysica Acta, vol. 289 (1972) pp. 276–283.

Primary Examiner—Lionel M. Shapiro
Attorney, Agent, or Firm—Ladas & Parry

[57] ABSTRACT

Cu,Zn-superoxide dismutase is recovered from yeast by plasmolysis with a small amount of ether or any other water immiscible, organic solvent and subsequent autolysis in water at a temperature of 25° to 50° C. and pH 5 to 9, following which the precipitate is removed and the superoxide dismutase is purified and isolated from the residual liquid, in particular by chromatography on carboxymethyl cellulose at pH 4.7 to 5.5.

Cu,Zn-superoxide dismutase from *Saccharomyces cerevisiae* has the amino acid sequence:

$$\underset{1}{\text{Val}}-\text{Gln}-\text{Ala}-\text{Val}-\underset{5}{\text{Ala}}-\text{Val}-\text{Leu}-\text{Lys}-\text{Gly}-\underset{10}{\text{Asp}}-$$

$$\text{Ala}-\text{Gly}-\text{Val}-\text{Ser}-\underset{15}{\text{Gly}}-\text{Val}-\text{Val}-\text{Lys}-\text{Phe}-\underset{20}{\text{Glu}}-$$

$$\text{Gln}-\text{Ala}-\text{Ser}-\text{Glu}-\underset{25}{\text{Ser}}-\text{Glu}-\text{Pro}-\text{Thr}-\text{Thr}-\underset{30}{\text{Val}}-$$

$$\text{Ser}-\text{Tyr}-\text{Glu}-\text{Ile}-\underset{35}{\text{Ala}}-\text{Gly}-\text{Asn}-\text{Ser}-\text{Pro}-\underset{40}{\text{Asn}}-$$

$$\text{Ala}-\text{Glu}-\text{Arg}-\text{Gly}-\underset{45}{\text{Phe}}-\text{His}-\text{Ile}-\text{His}-\text{Glu}-\underset{50}{\text{Phe}}-$$

$$\text{Gly}-\text{Asp}-\text{Ala}-\text{Thr}-\underset{55}{\text{Asn}}-\text{Gly}-\text{Cys}-\text{Val}-\text{Ser}-\underset{60}{\text{Ala}}-$$

$$\text{Gly}-\text{Pro}-\text{His}-\text{Phe}-\underset{65}{\text{Asn}}-\text{Pro}-\text{Phe}-\text{Lys}-\text{Lys}-\underset{70}{\text{Thr}}-$$

$$\text{His}-\text{Gly}-\text{Ala}-\text{Pro}-\underset{75}{\text{Thr}}-\text{Asp}-\text{Glu}-\text{Val}-\text{Arg}-\underset{80}{\text{His}}-$$

$$\text{Val}-\text{Gly}-\text{Asp}-\text{Met}-\underset{85}{\text{Gly}}-\text{Asn}-\text{Val}-\text{Lys}-\text{Thr}-\underset{90}{\text{Asp}}-$$

$$\text{Glu}-\text{Asn}-\text{Gly}-\text{Val}-\underset{95}{\text{Ala}}-\text{Lys}-\text{Gly}-\text{Ser}-\text{Phe}-\underset{100}{\text{Lys}}-$$

$$\text{Asp}-\text{Ser}-\text{Leu}-\text{Ile}-\underset{105}{\text{Lys}}-\text{Leu}-\text{Ile}-\text{Gly}-\text{Pro}-\underset{110}{\text{Thr}}-\text{Ser}-$$

$$\text{Val}-\text{Val}-\text{Gly}-\underset{115}{\text{Arg}}-\text{Ser}-\text{Val}-\text{Val}-\text{Ile}-\underset{120}{\text{His}}-\text{Ala}-$$

$$\text{Gly}-\text{Gln}-\text{Asp}-\underset{125}{\text{Asp}}-\text{Leu}-\text{Gly}-\text{Lys}-\text{Gly}-\underset{130}{\text{Asp}}-\text{Thr}-$$

$$\text{Glu}-\text{Glu}-\text{Ser}-\underset{135}{\text{Leu}}-\text{Lys}-\text{Thr}-\text{Gly}-\text{Asn}-\underset{140}{\text{Ala}}-\text{Gly}-$$

$$\text{Pro}-\text{Arg}-\text{Pro}-\underset{145}{\text{Ala}}-\text{Cys}-\text{Gly}-\text{Val}-\text{Ile}-\underset{150}{\text{Gly}}-$$

Leu—Thr—Asn where Cys-57 and Cys-146 form a disulfide bond.

6 Claims, No Drawings

PROCESS FOR RECOVERING Cu,Zn-SUPEROXIDE DISMUTASE FROM YEAST

The present invention relates to a novel process for recovering Cu,Zn-superoxide dismutase (SOD) from yeast.

Superoxide dismutases are enzymes catalyzing the dismutation of the superoxide radical, $O_2^-$, to oxygen and hydrogen peroxide:

$$2O_2^- + 2H^+ \rightarrow H_2O_2 + O_2$$

Since 1969 enzymes having this property have been isolated from a large number of different organisms.

Superoxide dismutases containing copper and zinc in their active sites are found in the cytoplasma of eukaryotes. It has been found that these enzymes are dimeric molecules which exhibit a very high degree of homology in their amino acid sequence (C. Petersen et al., Carlsberg Res. Commun. Vol 42, p. 391–395, 1977) and have related physico-chemical properties (A.E.G. Cass et al., Carlberg Res. Cummun. Vol. 43, p 439–449, 1978). Another class of superoxide dismutases containing iron or manganese in their active sites are found in prokaryotes and in eukaryotic mitochondria. In this class there is also a high similarity in amino acid composition and N-terminal amino acid sequence. However, there is no significant homology between the two classes of superoxide dismutases.

The function of the superoxide dismutases is apparently to protect the cells in aerobic organisms against the toxic effects of the superoxide radical, which is a byproduct of the reaction of oxygen in the organism. It is believed that the superoxide radical is involved in various inflammatory processes in the tissues and that it contributes to causing rheumatoid arthritis. It has therefore been proposed to use superoxide dismutase for treating inflammations and perhaps rheumatoid arthritis. The therapeutic effect of Cu, Zn-superoxide dismutase on inflammatory diseases has been confirmed by experiments. It would accordingly be of great importance if it were possible to provide a process for recovering Cu,Zn-superoxide dismutase on an industrial scale in a high yield.

Among the Cu,Zn-superoxide dismutases the bovine enzyme is the most studied. Thus, the complete amino acid sequence and X-ray structure of this enzyme are known. Also, it has been investigated by a variety of spectroscopic methods.

Goscin and Fridovich (Biochim. Biophys. Acta 289, p. 276–283, 1972) recovered Cu,Zn-superoxide dismutase from yeast by the so-called two-phase method, in which after freezing and thawing the yeast cake was stirred in approximately the same volume of a mixture of ethanol and chloroform in the volume ratio of 5:3 for some hours at 25° C., following which the mixture was centrifuged, the clear supernatant was admixed with solid $K_2HPO_4$ and the organic phase salted out was isolated and clarified by centrifugation. Then the proteings were precipitated by adding cold acetone, the precipitate was redissolved in cold phosphate buffer of pH 7,8 and purified of brownish impurities with microgranular diethylamino ethyl cellulose ("DE-32"), and the pale green filtrate was dialyzed against phosphate buffer of pH 7,8 and after clarification by centrifugation chromatographed on a column of "DE-32".

This process and various variants of it are convenient, giving a high yield of enzyme when working on a small scale. However, the process becomes very inappropriate when more than 3 or 4 kg of yeast cake are to be treated; in particular, the extraction step requires large amounts of solvents and is cumbersome and time-consuming. On an industrial scale the two-phase process is very uneconomic and not useful in practice.

The object of the present invention is to provide a simple and economic process for recovering Cu,Zn-superoxide dismutase from yeast which is useful on an industrial scale and gives at least just as high yields of the enzyme as the known processes.

This is achieved according to the invention by using the property of water immiscible, organic solvents, particularly ether, that in small amounts they activate enzymes in the yeast cell and cause at the same time the cell wall to break down (plasmolysis).

Accordingly, the process of the invention is characterized by subjecting the yeast to plasmolysis by adding a small amount of water immiscible, organic solvent, preferably ether, and to subsequent autolysis in water at a temperature of 25° to 50° C. and a pH in the range of 5 to 9, and then removing the precipitate and purifying and isolating the superoxide dismutase from the residual liquid (the SOD fraction).

As regards the subsequent purification of SOD it has been found particularly advantageous that the autolysis takes place at a temperature of about 45° C. and a pH of 7 to 8.

According to the invention a particularly effective removal of undesirable proteins after autolysis is achieved by adjusting the pH of the suspension to 4.0 to 5.5 and removing the precipitate by centrifugation or filtration.

After removal of the precipitate SOD may be purified and isolated from the SOD fraction in a usual manner by ion exchange chromatography on slightly acid or slightly basic cellulose or polysaccharide ion exchange resins, e.g. DEAE cellulose.

According to the invention a particularly pure final product and increased capacity of the ion exchange resin in a subsequent ion exchange chromatography is achieved by removing low molecular impurities from the SOD fraction by diafiltration before isolation of SOD, i.e., by a combination of dialysis and ultrafiltration.

According to the invention it has been found that a particularly good separation of SOD from other present proteins is achieved when the SOD fraction is purified by ion exchange chromatography on carboxymethyl cellulose at a pH of about 4.8. This is actually at variance with the theory, according to which ion exchange resins were only to exhibit affinity to substances of opposite polarity. However, carboxymethyl cellulose and SOD have the same polarity in the pH range used here, and it is therefore surprising that good results are obtained with this embodiment of the process.

From the Danish Pat. No. 131 091 which deals with the recovery of superoxide dismutase from bovine liver it is known to purify the enzyme by passing a solution of the enzyme in a buffer solution of an ionic strength of up to $10^{-2}$ molar concentration and a pH of 5.5 to 8 over a column of an ion exchange resin with either slightly basic or acid groups which attract ions of opposite polarity. One of the general examples of useful resins mentioned is carboxymethyl cellulose, but at pH 5.5 to 8 it has not, as required in the claim, an opposite polarity of SOD, and further the patent provides no examples of the use of carboxymethyl cellulose.

After purification of the SOD fraction by ion exchange chromatography the active fractions of the eluate may be further purified in a known manner by gel filtration or fractional alcohol precipitation and be subjected to one or more additional chromatographies, preferably on carboxymethyl cellulose, following which the active fractions are dialyzed against distilled water and concentrated to dryness, preferably by freeze drying.

After extraction of Cu,Zn-superoxide dismutase from Saccharomyces cerevisiae by the process of the invention, it has been found by continued studies that the isolated enzyme contains two peptide chains of the following amino acid sequence:

Val—Gln—Ala—Val—Ala—Val—Leu—Lys—Gly—Asp—

Ala—Gly—Val—Ser—Gly—Val—Val—Lys—Phe—Glu—

Gln—Ala—Ser—Glu—Ser—Glu—Pro—Thr—Thr—Val—

Ser—Tyr—Glu—Ile—Ala—Gly—Asn—Ser—Pro—Asn—

Ala—Glu—Arg—Gly—Phe—His—Ile—His—Glu—Phe—

Gly—Asp—Ala—Thr—Asn—Gly—Cys—Val—Ser—Ala—

Gly—Pro—His—Phe—Asn—Pro—Phe—Lys—Lys—Thr—

His—Gly—Ala—Pro—Thr—Asp—Glu—Val—Arg—His—

Val—Gly—Asp—Met—Gly—Asn—Val—Lys—Thr—Asp—

Glu—Asn—Gly—Val—Ala—Lys—Gly—Ser—Phe—Lys—

Asp—Ser—Leu—Ile—Lys—Leu—Ile—Gly—Pro—Thr—Ser—

Val—Val—Gly—Arg—Ser—Val—Val—Ile—His—Ala—

Gly—Gln—Asp—Asp—Leu—Gly—Lys—Gly—Asp—Thr—

Glu—Glu—Ser—Leu—Lys—Thr—Gly—Asn—Ala—Gly—

Pro—Arg—Pro—Ala—Cys—Gly—Val—Ile—Gly—

Leu—Thr—Asn where Cys-57 and Cys-146 form a disulfide bond.

The process of the invention is illustrated more fully in the following example.

EXAMPLE 2.5 l of diethyl ether were added to 20 kg of bakers' yeast (Saccharomyces cerevisiae) and the mixture was left for 30 minutes to make stirring possible. After stirring for about 2 hours at 25° C. 20 l of hot water were added, pH was adjusted to 7.5 and stirring was continued for 4 hours at 45° C. After stirring for another 16 hours with a drop in temperature to 25° C. pH was adjusted to 4.8 and the suspension was clarified by centrifugation at 2000 G for 30 minutes. To remove low molecular weight compounds the supernatant was diluted 5-fold with 0.01 M sodium acetate buffer at pH 4.8 and concentrated to 10 l by ultrafiltration. The latter procedure was performed twice.

1 l of microgranular carboxymethyl cellulose (available under the name "CM-52" from Whatman Ltd) which had been equilibrated with 0.025 M sodium acetate buffer at pH 4.8 was added to the concentrated solution, and the mixture was stirred for 1 hour. The carboxymethyl cellulose was collected on a column of 30 cm diameter, washed with 10 l of 0.025 M sodium acetate buffer at pH 4.8, and transferred to a column of 10 cm diameter. The column was eluted with a linear gradient of sodium acetate (0.025→0.200 M) at pH 4.8 in a total volume of 6 l. The flow rate was 400 ml/h and fractions of 30 ml were collected. The active fractions which were intensively red were collected and the pool was concentrated by ultrafiltration before freeze drying.

The freeze-dried sample was redissolved in 50 ml of 0.025 M sodium acetate buffer at pH 4.8 and applied to a 5×40 cm column of dextrangel (available under the name "Sephadex G-50 superfine" from Pharmacia Fine Chemicals AB) equilibrated against the acetate buffer. The column was eluted with 1 l of 0.025 M sodium acetate at pH 4.8 and fractions of 5 ml were collected. The flow rate was 110 ml/h.

A visible result of the gel chromatography was that the green Cu,Zn-superoxide dismutase separated from the red heme protein, although the two bands were lying very close.

The active fractions were pooled and applied to a 5×10 cm column of "CM-52" equilibrated with 0.025 M sodium acetate pH 4.8. The column was eluted with a linear gradient of sodium acetate (0.025→0.200 M) at pH 4.8. A total volume of 1200 ml was applied with a flow rate of 200 ml/h, and fractions of 6 ml were collected. The active fractions were pooled, dialyzed against distilled water, and freeze dried.

The gel filtration step can be replaced by an alcohol precipitation step. The freeze dried sample from the "CM-52" batch step is dissolved in 100 ml of 0.005 M potassium phosphate buffer at pH 7.0 and 67 ml of ethanol are slowly added. After 10 minutes centrifugation at 13000 r.p.m. another 166 ml of ethanol are added to the supernatant. The precipitate is collected by centrifugation for 15 minutes at 13000 r.p.m. and redissolved in 50 ml of 0.025 M sodium acetate buffer at pH 4.8. The sample is then applied to a "CM-52" column as described above, and the active fractions are dialyzed against distilled water and freeze-dried. The results of the purification procedure are summarized in the following table.

TABLE

| Fraction | Purification of Cu, Zn-superoxide dismutase from 20 kg of yeast | | | | | | | |
|---|---|---|---|---|---|---|---|---|
| | Protein conc. (mg/ml) | Total volume (ml) | Total protein (mg) | Activity (units/ml) | Total units | Yield (%) | Specific activity (units/mg) | Fold purication |
| Lysate, pH 4.8 | 20 | 28000 | 560000 | 1090 | 3,05 × 10$^7$ | 100 | 55 | 1 |
| Concentrate from ultrafiltration | 18,1 | 17000 | 308000 | 962 | 1,64 × 10$^7$ | 54 | 53 | 1 |

TABLE-continued

| Fraction | Protein conc. (mg/ml) | Total volume (ml) | Total protein (mg) | Activity (units/ml) | Total units | Yield (%) | Specific activity (units/mg) | Fold purication |
|---|---|---|---|---|---|---|---|---|
| Comb. fractions from "CM-52" batch | 2,0 | 985 | 1970 | 12600 | $1,24 \times 10^7$ | 41 | 6300 | 115 |
| Comb. fractions from "G-50 superfine" | 15,0 | 95 | 1420 | $1,29 \times 10^5$ | $1,22 \times 10^7$ | 40 | 8600 | 156 |
| Comb. fractions from "CM-52" column | 5,48 | 208 | 1140 | $5,06 \times 10^4$ | $1,05 \times 10^7$ | 34 | 9230 | 168 |
| Alternative procedure: | | | | | | | | |
| Redissolved alcohol precipitate | 27,3 | 50 | 1360 | $2,20 \times 10^5$ | $1,10 \times 10^7$ | 36 | 8090 | 147 |
| Comb. fractions from "CM-52" column | 8,07 | 132 | 1070 | $7,51 \times 10^4$ | $9,91 \times 10^6$ | 32 | 9300 | 169 |

I claim:

1. A process for recovering Cu,Zn-superoxide dismutase (SOD) from yeast, characterized by subjecting the yeast to plasmolysis by adding a small amount of ether, and to subsequent autolysis in water at a temperature of 25° to 50° C. and a pH in the range of 5 to 9, and then removing the precipitate and purifying and isolating the superoxide dismutase from the residual liquid (the SOD fraction).

2. A process according to claim 1, characterized by the fact that the autolysis takes place at a temperature of about 45° C. and a pH value of 7 to 8.

3. A process according to claim 1 or 2, characterized by removing undesirable proteins by adjusting the pH of the autolysis suspension to 4.0 to 5.5 and removing the precipitate by centrifugation or filtration.

4. A process according to claim 1 or claim 2, characterized by removing the low molecular impurities from the SOD fraction by diafiltration.

5. A process according to claim 1 or claim 2, characterized by purifying the SOD fraction by ion exchange chromatography on carboxymethyl cellulose at a pH of about 4.8.

6. A process according to claim 1 or claim 2, characterized by producing superoxide dismutase from Saccharomyces cerevisiae of the amino acid sequence:

$\overset{1}{\text{Val}}$—Gln—Ala—Val—$\overset{5}{\text{Ala}}$—Val—Leu—Lys—Gly—$\overset{10}{\text{Asp}}$—

Ala—Gly—Val—Ser—$\overset{15}{\text{Gly}}$—Val—Val—Lys—Phe—$\overset{20}{\text{Glu}}$—

Gln—Ala—Ser—Glu—$\overset{25}{\text{Ser}}$—Glu—Pro—Thr—Thr—$\overset{30}{\text{Val}}$—

Ser—Tyr—Glu—Ile—$\overset{35}{\text{Ala}}$—Gly—Asn—Ser—Pro—$\overset{40}{\text{Asn}}$—

Ala—Glu—Arg—Gly—$\overset{45}{\text{Phe}}$—His—Ile—His—Glu—$\overset{50}{\text{Phe}}$—

Gly—Asp—Ala—Thr—$\overset{55}{\text{Asn}}$—Gly—Cys—Val—Ser—$\overset{60}{\text{Ala}}$—

Gly—Pro—His—Phe—$\overset{65}{\text{Asn}}$—Pro—Phe—Lys—Lys—$\overset{70}{\text{Thr}}$—

His—Gly—Ala—Pro—$\overset{75}{\text{Thr}}$—Asp—Glu—Val—Arg—$\overset{80}{\text{His}}$—

Val—Gly—Asp—Met—$\overset{85}{\text{Gly}}$—Asn—Val—Lys—Thr—$\overset{90}{\text{Asp}}$—

Glu—Asn—Gly—Val—$\overset{95}{\text{Ala}}$—Lys—Gly—Ser—Phe—$\overset{100}{\text{Lys}}$—

Asp—Ser—Leu—Ile—$\overset{105}{\text{Lys}}$—Leu—Ile—Gly—Pro—$\overset{110}{\text{Thr}}$—Ser—

Val—Val—Gly—$\overset{115}{\text{Arg}}$—Ser—Val—Val—Ile—$\overset{120}{\text{His}}$—Ala—

Gly—Gln—Asp—$\overset{125}{\text{Asp}}$—Leu—Gly—Lys—Gly—$\overset{130}{\text{Asp}}$—Thr—

Glu—Glu—Ser—$\overset{135}{\text{Leu}}$—Lys—Thr—Gly—Asn—$\overset{140}{\text{Ala}}$—Gly—

Pro—Arg—Pro—$\overset{145}{\text{Ala}}$—Cys—Gly—Val—Ile—$\overset{150}{\text{Gly}}$—

Leu—Thr—Asn where Cys-57 and Cys-146 form a fisulfide bond.

* * * * *